United States Patent [19]

Barcza

[11] 4,374,130
[45] Feb. 15, 1983

[54] 4,4'-(ALKANEDIYL)-BIS(2,2,6,6-TETRAALKYL-1-OXA-4-AZA-2,6-DISILACYCLOHEXANES)

[75] Inventor: Sandor Barcza, Mountain Lakes, N.J.

[73] Assignee: Sandoz, Inc., East Hanover, N.J.

[21] Appl. No.: 227,179

[22] Filed: Jan. 22, 1981

Related U.S. Application Data

[62] Division of Ser. No. 173,459, Jul. 30, 1980, abandoned.

[51] Int. Cl.³ .......................................... A61K 31/695
[52] U.S. Cl. ..................................... 424/184; 556/408
[58] Field of Search ......................... 424/184; 556/408

[56] References Cited

PUBLICATIONS

Berichte, 94, 6-1-61, pp. 1585-1591.

Primary Examiner—Frederick E. Waddell

Attorney, Agent, or Firm—Gerald D. Sharkin; Robert S. Honor; Joseph J. Borovian

[57] ABSTRACT

This disclosure describes compounds of the formula

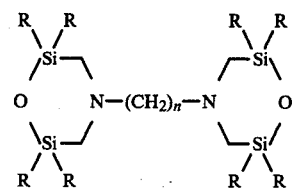

wherein
 n is 3, 5 or 7, and
 each R is lower alkyl having 1 to 4 carbon atoms, or pharmaceutically acceptable acid addition salts thereof, which are useful as anti-diabetic agents in particular glucagon inhibiting agents.

3 Claims, No Drawings

4,4'-(ALKANEDIYL)-BIS(2,2,6,6-TETRAALKYL-1-OXA-4-AZA-2,6-DISILACYCLOHEXANES)

This is a continuation, of application Ser. No. 173,459 filed July 30, 1980, now abandoned.

This invention relates to 4,4'-(alkanediyl) bis (2,2,6,6-tetraalkyl-1-oxa-4-aza-2,6-disilacyclohexanes) which exhibit anti-diabetic activity. In particular, it relates to 4,4'-(alkanediyl)-bis(2,2,6,6-tetraalkyl-1-oxa-4-aza-2,6-disilocyclohexanes) and pharmaceutically acceptable acid addition salts which are useful as glucagon inhibiting agents.

The compounds of this invention may be represented by the following structural formula

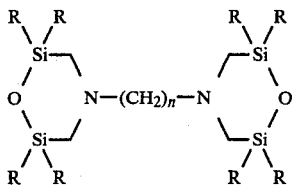

wherein
n is 3, 5 or 7, and
each R is lower alkyl, i.e., alkyl having 1 to 4 carbon atoms, e.g., methyl, ethyl and the like.

The compounds of formula (I) are prepared according to the following reaction scheme:

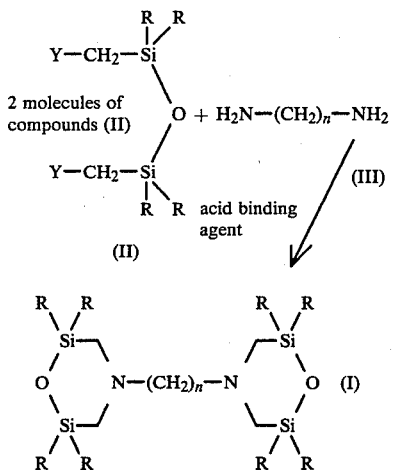

wherein
Y is a leaving group such as an arylsulfonate or alkylsulfonate, e.g., tosylate or mesylate or iodo, bromo or chloro, preferably iodo, and
n and R are as defined above.

The compounds of formula (I) are prepared by reacting two molecules of a compound of formula (II) with a compound of the formula (III) in the presence of an acid binding agent. Although the particular acid binding agent employed is not critical, the preferred acid binding agents include triethylamine, diisopropylmethylamine, alkali metal hydroxides or hydrides such as potassium hydroxide, sodium hydroxide, lithium hydride and the like, especially triethylamine. The reaction may be carried out without a solvent, however, aprotic solvents such as acetonitrile, dimethylformamide, dimethylacetamide and protic solvents such as the lower alkanols, e.g., methanol, ethanol and the like, may be employed if the use of a solvent is desired. The temperature of the reaction is not critical, but it is preferred that the reaction be run from about $-10°$ to $100°$ C., preferably from about $20°$ to $30°$ C. The reaction is run from about 4 to 200 hours, preferably from 12 to 36 hours. The product is recovered using conventional techniques, e.g., extraction and evaporation followed by distillation.

Many of the compounds of formulae (II) and (III) are known and may be prepared by methods described in the literature. The compounds of formulae (II) and (III) not specifically described in the literature may be prepared by analogous methods from known starting materials.

The preferred compounds of formula (I) are the compounds wherein each R group represents methyl and n is 3.

The compounds of formula (I) are useful because they possess pharmacological activity in animals as glucagon inhibiting agents in the treatment of diabetes as indicated (1) by lowering of the plasma glucagon levels in the alloxan diabetic rats. In this test, adult male rats each weighing between 250 and 350 g. are injected intraveneously with 40 mg/kg of alloxan and, after 5 days, are tested for the presence of urinary glucose (clinistix). The selection of animals is determined according to the degree of urine clinistix reaction, i.e., only animals with a positive urine response (deep purple color of clinistix within 15 seconds) are used. The rats are divided into 12 treatment groups and are dosed orally with 100 mg/kg body weight of the test compound. After two hours, the animals in each group are sacrificed and 5 mls. of blood are collected and the plasma separated. The plasma is stored frozen until assayed for glucagon, at which time plasma levels of glucagon are determined using radioimmunological techniques. Similar tests are run simultaneously with a "negative control" group comprising non-diabetic rats and a "positive control" group comprising rats which received only the alloxan; and (2) by lowering the plasma glucagon levels in alloxan diabetic dogs. In this test, male beagles weighing 8 to 12 kilograms are made diabetic by injecting them intravenously with 75 mg/kg of alloxan. In each test, 4 dogs are studied for one week and are subjected to the following schedule. On Sunday morning, the first day of the tests, the dogs are given a long-acting dose of insulin (NPH Iletin) at which no ketones appear in the urine and body weight is stabilized. Food is then withdrawn at 12:00 noon and the dogs are fasted overnight. On Monday through Friday, each dog receives two bags of "Top Choice" commercial dog food, one at 9:00 a.m. and the other at 3:30 p.m. At 3:30 p.m. each dog receives its appropriate dose of insulin in the short acting form and food is again withheld overnight until the next morning. On Monday, no blood samples are taken and the dogs are allowed to acclimate themselves to the feeding schedule. On Tuesday through Friday, peripheral blood samples are obtained at the following times: 8:00, 9:00, 9:30, 10:00, 11:00, 12:00, 2:00 and 3:00. On Thursday, 60 mg/kg of the test compound is administered orally in a gelatin capsule at 8:30 a.m.

The blood samples are analyzed for glucagon by radio immunological techniques and glucose (where necessary) by colorimetric methods. The criteria for judging the activity of the test compound is its ability to suppress the meal-induced glucagon rise on the day of treatment when compared to the day prior to treatment (Wednesday) and the day after (Friday). This test is based upon the principle that in the diabetic dog, ingestion of a standardized meal following an overnight fast results in a 2 to 5 increase in glucagon levels for 3 to 5 hours.

The anti-diabetic effective dosage of a compound of formula (I), or a pharmaceutically acceptable salt thereof, employed as a glucagon inhibiting agent in lowering the glucagon levels in plasma may vary depending on the particular compound employed, the mode of administration and the severity of the condition being treated. However, in general, satisfactory results as a glucagon inhibiting agent in lowering the glucagon levels in plasma are obtaind when a compound of formula (I), or a pharmaceutically acceptable acid addition salt thereof, is administered at a daily dosage of from about 10 milligrams to about 250 milligrams per kilogram of animal body weight, preferably given orally and in divided doses three times a day, more preferably, before each meal, or in sustained release form. For most large mammals, the total daily dosage is from about 300 milligrams to about 2000 milligrams. Unit dosage forms suitable for internal use comprise from about 75 to 1000 milligrams of the active compound in intimate admixture with a solid or liquid, pharmaceutically acceptable carrier.

For the above-mentioned use, the compounds may be administered orally in such forms as tablets, capsules, elixirs, suspensions and the like or parenterally in the form of an injectable solution(s) or suspensions(s). The dosage will vary depending upon the mode of administration utilized and the compound employed.

The compounds of formula (I) may be similarly administered in the form of their non-toxic pharmaceutically acceptable salts. Such salts possess the same order of activity as the non-salt form and are readily prepared by reacting the molecule with an appropriate acid or an appropriate base by conventional techniques, and, accordingly, are included within the scope of this invention. Representative of such salts are the mineral acid salts, e.g., hydrochloride, hydrobromde, sulfate and the like.

Tablets and capsules containing the ingredients indicated below may be useful as glucagon inhibiting agents in treatment of diabetes in divided doses three times per day, preferably before each meal:

| Ingredients | Weight (mg.) Tablet | Capsule |
| --- | --- | --- |
| 4,4'-(1,3-propanediyl) bis (2,2,6,6-tetramethyl-1-oxa-4-aza-2,6-disilacyclohexane) | 300 | 300 |
| tragacanth | 10 | — |
| lactose | 247.5 | 300 |
| corn starch | 25 | — |
| talcum | 15 | — |
| magnesium stearate | 2.5 | — |
| | 600 mg. | 600 mg. |

EXAMPLE 1

4,4'-(1,3-propanediyl) bis (2,2,6,6-tetramethyl-1-oxa-4-aza-2,6-disilacyclohexane)

To a round flask with magnetic stirrer and external ice cooling there is added at a temperature of 0° C. over a period of 3 minutes with stirring 82.8 g. (0.2 mole) of 1,3-bis-iodomethyl-1,1,3,3-tetramethyl-disiloxane, 7.4 g. (0.1 mole) of 1,3-diamino-propane and 50 g. (approx. 0.5 mole) of triethylamine. While stirring the resulting mixture is then allowed to come to room temperature overnight while the ice is melting. The reaction is then stirred for an additional seven days at room temperature, followed by a half-hour reflux and overnight standing. (Note: reaction may be completed in 12 to 36 hours.) The resulting mixture containing two liquid phases plus crystals is then distributed between approximately 0.5 l. of 1:1 ether:hexane and 0.5 l. water, the aqueous phase is extracted with one more portion of ether:hexane and with hexane. The combined organic phase is washed twice with water and concentrated under vacuum to give 35.2 g. of a crude oily product. This crude product is then vacuum distilled through a Vigreux column to give 23.4 g. of 4,4'-(1,3-propanediyl) bis (2,2,6,6-tetramethyl-1 oxa-4-aza-2,6-disilacyclohexane); b.p. 100° to 105° C. at 0.5 mm Hg.

The dihydrochloride salt of the title compound is prepared in the following manner.

To 4 ml. of aqueous concentrated hydrochloric acid (approximately 40 m mol) in 50 ml. of cold acetone there is added 15.7 mg. (40 m mol) of 4,4'-(1,3- propanediyl) bis (2,2,6,6-tetramethyl-1-oxa-4-aza-2,6-disilacyclohexane). in 150 ml. of acetone while stirring. The pH is slightly basic, whereupon an additional 4 ml. (approximately 40 m mol) of concentrated hydrochloric acid in approximately 100 ml. of acetone is added. Stirring is continued for ½ hour. The resulting slurry is then filtered, and the precipitate then washed twice with acetone and dried at 70° to 80° C. in vacuo overnight to give the dihydrochloride; m.p. 275° to 280° C. (dec).

Following the above procedure and using in place of 1,3-diamino-propane an equivalent amount of
 (a) 1,5-diamino-pentane, or
 (b) 1,7-diamino-heptane
there is obtained
 (a) 4,4'-(1,5-pentanediyl) bis(2,2,6,6-tetramethyl-1-oxa-4-aza-2,6-disilacyclohexane), or
 (b) 4,4'-(1,7-heptanediyl) bis(2,2,6,6-tetramethyl-1-oxa-4-aza-2,6-disilacyclohexane), respectively.

The 4,4'-(1,3-propanediyl) bis(2,2,6,6-tetramethyl-1-oxa-4aza-2,6-disilacyclohexane) of this example is an effective glucagon inhibiting agent when orally administered to an animal in need of said treatment at a dosage of 300 mg. three times per day, preferably before each meal.

The 4,4'-(1,3-propanediyl) bis (2,2,6,6-tetramethyl-1-oxa-4-aza-2,6-disilacyclohexane) has a minimum effective dose in test 1) of 30 mg/kg and in test 2) of 60 mg/kg.

EXAMPLE 2

Following the procedure of Example 1, but using in place of 1,3-bis-iodomethyl-1,1,3,3-tetramethyl-disiloxane, 46.2 g. (0.2 mole) of 1,3-bis-chloromethyl-1,1-3,3-tetramethyl-disiloxane there is obtained 4,4'-(1,3-propanediyl) bis (2,2,6,6-tetramethyl-1-oxa-4-aza-2,6-disilacyclohexane).

It should be noted that the 1,3-bis-chloromethyl-1,1,3,3-tetramethyl-disiloxane may be converted if desired to the 1,3-bis-iodomethyl-1,1,3,3-tetramethyl-disiloxane starting material of Example 1 by reacting said bis-chloro compound with sodium iodide, externally or in situ.

What is claimed is:

1. A pharmaceutical composition for inhibiting glucagon which comprises a glucagon inhibiting effective amount of a compound of the formula,

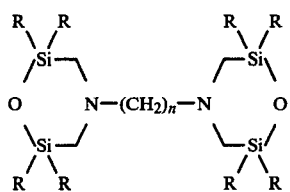

wherein
each R, independently, is $C_{1-4}$-alkyl, and
n is an integer 3, 5 or 7,
or a pharmaceutically acceptable salt thereof, and a pharmaceutically acceptable carrier.

2. A method of inhibiting glucagon which comprises administering to a mammal in need of said treatment a glucagon inhibiting effective amount of a compound of the formula,

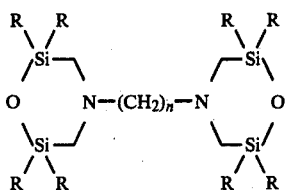

wherein
each R, independently, is $C_{1-4}$-alkyl, and
n is an integer 3, 5 or 7,
or a pharmaceutically acceptable salt thereof.

3. A method of inhibiting glucagon according to claim 2 which comprises administering to a mammal in need of said treatment a glucagon inhibiting effective amount of the compound 4,4'-(1,3-propanediyl) bis(2,2,6,6-tetramethyl-1oxa-4-aza-2,6-disilacyclohexane).

* * * * *

UNITED STATES PATENT AND TRADEMARK OFFICE
CERTIFICATE OF CORRECTION

PATENT NO. : 4,374,130
DATED : February 15, 1983
INVENTOR(S) : Sandor Barcza

It is certified that error appears in the above—identified patent and that said Letters Patent is hereby corrected as shown below:

Title page, Item [62]; change "Division" to -- Continuation --.

Signed and Sealed this

Thirty-first Day of May 1983

[SEAL]

Attest:

DONALD J. QUIGG

Attesting Officer        Acting Commissioner of Patents and Trademarks